(12) United States Patent
Reuter

(10) Patent No.: US 6,852,831 B2
(45) Date of Patent: Feb. 8, 2005

(54) ALKYLENEDIOXYTHIOPHENES AND POLY (ALKYLENEDIOXYTHIOPHENE)S HAVING URETHANE-CONTAINING SIDE GROUPS

(75) Inventor: Knud Reuter, Krefeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/409,241

(22) Filed: Apr. 8, 2003

(65) Prior Publication Data

US 2003/0216540 A1 Nov. 20, 2003

(30) Foreign Application Priority Data

Apr. 10, 2002 (DE) .......................................... 102 15 706

(51) Int. Cl.$^7$ .............................................. C08G 75/00
(52) U.S. Cl. ......................... 528/380; 528/49; 528/73; 528/74; 528/425
(58) Field of Search .......................... 528/380, 49, 73, 528/74, 425

(56) References Cited

U.S. PATENT DOCUMENTS 5,111,327 A  5/1992  Blohm et al. ............... 526/256

OTHER PUBLICATIONS

Adv.Mater. (month unavailable) 2000, 12, No. 7, pp. 481–494, Poly(3,4–ethylenedioxythiophene) and Its Derivatives: Past, Present, and Future** By L. "Bert" Groenendaal,* Friedrich Jonas, Dieter Freitag, Harald Pielartzik, and John R. Reynolds.
Adv. Mater. (month unavailable) 1999, 11, No. 16, pp. 1379–1382, Enhanced Contrast Ratios and Rapid Switching in Electrochromics Based on Poly(3,4–propylenedioxythiophene) Derivatives** By Dean M. Welsh, Anil Kumar, E.W. Meijer, and John R. Reynolds*.
Polym. Prepr. (Am. Chem Soc., Div. Polym. Chem.) 38(2), (month unavailable) (1997), pp. 320 "Easily Functionalized 3,4–Ethylenedioxythiophene" by Dean M. Walsh et al.
Kros, A et al, "Poly(3,4–ethylenedioxythiophene)–based copolymers for biosensor applications" Jounral of Polymer Science: Part A: Polymers Chemistry, Wiley Periodicals, Inc., Bd. 40, Nr. 6, Mar. 15, 2002, Seiten 738–747, XP002244145 *Seiten* 739, Spalte 2, Abstratz 2—Seite 740, Spalte 1, Absatz 3 * 8 Seite 741; Abbildung 1 *.

Schottlan, P., et al.: "Synthesis and Polymerization of New Monomers Derived from 3,4–Ethylenedioxythiophene" Journal De Chimie Physique, Societe De Chimie Physique, Paris, FR, Bd. 95, Nr. 6, 1998, Seiten 1258–1261 XP001013494 ISSN: 0021–7689 *Seite 1259*, Absatz 2* *Seite 1260; Abbildung 1* *Seite 1260, Absatz 2*.

Stephan O et al: "New Cation–Exchange Material Based on a Sulfonated 3,4–Ethylenedioxythiphene Monomer" Journal de Chimie Physique, Societe de Chimie Physique, Paris, FR, Bd. 95, Nr. 6, 1998, Seiten 1168–1171, XP000995727 ISSN: 0021–7689 *Seite 1169, Absatz 1* * Setien 1170, Abbildung 1*.

Kros A et al: "Poly(3,4–ethylenedioxythiophene)–based copolymers for biosensor applications" Journal of Polymer Science: Part A; Polymer Chemistry, Wiley Periodicals, Inc., Bd. 40, Nr. 6, Mar. 15, 2002, Seiten 738–747, XPOO2244145 Seite 739, Spalte 2, Absatz 2–Seite 740, Spalte 1, Absatz 3 * Seite 741; Abbildung 1*.

Schottland P et al: "Synthesis and Polymerization of New Monomers Derived From 3,4–Ethylenedioxythiophene" Journal de Chimie Physique, Societe de Chimie Physique, Paris, FR, Bd. 95, Nr. 6, 1998, Seiten 1258–1261, XPOO1013494 ISSN: 0021–7689 Seite 1259, Absatz 2 Seite 1260; Abbildung 1 * Seite 1260, Aabsatz 2*.

*Primary Examiner*—Duc Truong
(74) *Attorney, Agent, or Firm*—Diderico van Eyl; Godfried R. Akorli

(57) ABSTRACT

The present invention relates to alkylenedioxythiophenes of the formula I having urethane-containing side groups:

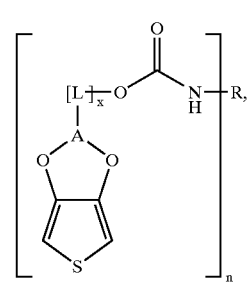

to their preparation and to their oligo- and polymeric derivatives (oligo- and poly(alkylenedioxythiophene)s).

19 Claims, No Drawings

ALKYLENEDIOXYTHIOPHENES AND POLY(ALKYLENEDIOXYTHIOPHENE)S HAVING URETHANE-CONTAINING SIDE GROUPS

BACKGROUND OF THE INVENTION

1. Field of the Invention

The invention relates to novel alkylenedioxythiophenes having urethane-containing side groups, to their preparation and to their oligo- and polymeric derivatives (oligo- and poly(alkylenedioxythiophene)s).

2. Brief Description of the Prior Art

The class of π-conjugated polymeric compounds has been the subject matter of numerous publications in the last few decades. They are also referred to as conductive polymers or as synthetic metals. Owing to the considerable delocalization of the π-electrons along the main chain, these polymers exhibit interesting (non-linear) optical properties and, after oxidation or reduction, and are also good electrical conductors. These compounds will consequently probably take on a leading and active role in various fields of practical application, for example in data storage, optical signal processing, suppression of electromagnetic interference (EMI) and solar energy conversion, and also in rechargeable batteries, light-emitting diodes, field-effect transistors, circuit boards, sensors and antistatic materials.

Examples of known π-conjugated polymers include polypyrroles, polythiophenes, polyanilines, polyacetylenes, polyphenylenes and poly(p-phenylene-vinylenes). A particularly important and industrially utilized polythiophene is poly-3,4-(ethylene-1,2-dioxy)thiophene which, in its oxidized form, has very high conductivities and is described, for example, in EP 339 340 A2. An overview of numerous poly(alkylenedioxythiophene) derivatives, in particular poly-3,4-(ethylene-1,2-dioxy)thiophene derivatives, their monomers, syntheses and applications is given by L. Groenendaal, F. Jonas, D. Freitag, H. Pielartzik & J. R. Reynolds, Adv. Mater. 12 (2000) 481–494. In U.S. Pat. No. 5,111,327 substituted 3,4-alkylenedioxythiophenes and also their conductive polymerization products are described.

Very high conductivities are also achieved by the methodology of in situ polymerization, in which the monomeric 3,4-(ethylene-1,2-dioxy)thiophene is reacted with oxidizing agents, for example iron-III tosylate, in solution to give a highly conductive layer of oxidized poly-3,4-(ethylene-1,2-dioxy)thiophene. This procedure is utilized, for example, for producing capacitors.

Despite the good properties of poly-3,4-(ethylene-1,2-dioxy)thiophene with regard to conductivity and processability, there is a need for further improvements, for example in conductivity, without impairments or even with improvements in colour and transparency, in electrochromic or else in mechanical properties.

Surprisingly, this object is achieved by the present invention.

SUMMARY OF THE INVENTION

The invention provides compounds of the formula I:

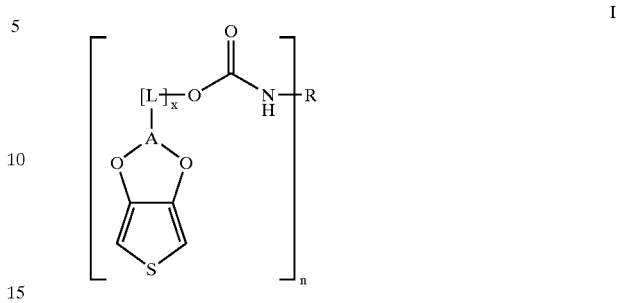

where

A is a $C_1$–$C_5$-alkylene radical which is optionally substituted at any desired point via a linker L by a urethane group and optionally bears further substituents, L is a methylene group, x is 0 or an integer of 1 or greater, preferably 0 or an integer from 1 to 6, more preferably 0 or 1, n is an integer from 1 to 4 and R is an n-valent linear or branched, optionally substituted, aliphatic $C_1$–$C_{22}$ radical, an n-valent, optionally substituted, cycloaliphatic $C_3$–$C_{12}$ radical or an n-valent, optionally substituted, aromatic $C_6$–$C_{14}$ radical, where, in the case that n is greater than 1, A and x may each independently be defined identically or differently.

The term "where, in the case that n is greater than 1, A and x may each independently be defined identically or differently" is to be understood as meaning that in the case that n is greater than 1, each A may independently be defined identically or differently and each x may independently be defined identically or differently.

A is preferably a methylene, ethylene or propylene radical which is optionally substituted at any desired point via a linker L by a urethane group, and optionally bears further substituents, preferably $C_1$–$C_{12}$-alkyl or aryl groups, where L is as defined as above.

DETAILED DESCRIPTION OF THE INVENTION

The invention preferably provides compounds of the formula II:

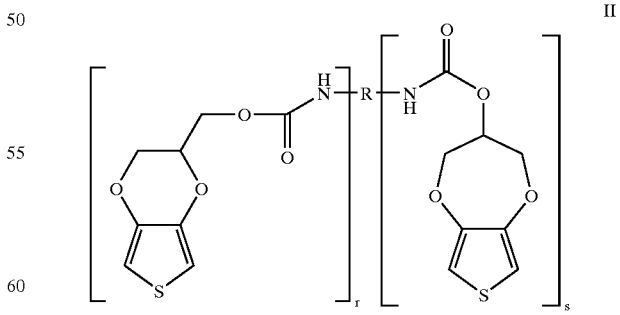

where

R is an n-valent linear or branched, optionally substituted, aliphatic $C_2$–$C_{22}$ radical, an n-valent, optionally substituted, cycloaliphatic $C_5$–$C_{12}$ radical or an n-valent, optionally substituted, aromatic $C_6$–$C_{14}$ radical, r and s are each independently integers from 0 to 4, with the proviso that r+s=n and n is an integer from 1 to 4.

These are more preferably compounds of the formula II where R is a linear, optionally substituted $C_6$–$C_{12}$-alkylene radical or an optionally substituted $C_6$–$C_{10}$-cycloalkylene radical, r and s are each independently integers from 0 to 2 and n=r+s=2.

These are more preferably compounds of the formulae IIa and IIb, corresponding to r=0 or s=0 in formula II:

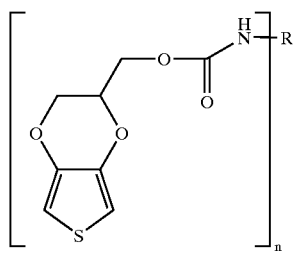

IIa

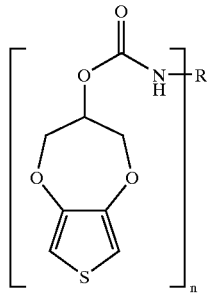

IIb where
R and n are each as defined above.

These are more preferably compounds of the formulae III and IV:

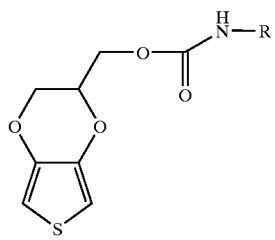

III

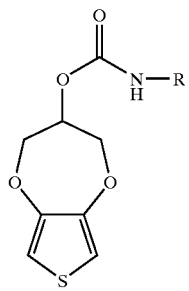

IV where
R is a linear or branched, optionally substituted, $C_1$–$C_{22}$-alkyl radical, an optionally substituted, $C_3$–$C_{12}$-cycloalkyl radical or an optionally substituted, $C_6$–$C_{14}$-aryl radical, preferably a linear $C_1$–$C_{12}$-alkyl radical or a $C_6$–$C_{10}$-cycloalkyl radical, more preferably a linear $C_4$–$C_{10}$-alkyl radical.

Substituents of the A and R radicals specified above and hereinbelow include all organic groups which have no hydrogen atoms reactive towards isocyanate groups, for example alkyl, cycloalkyl, aryl, halogen, ether, thioether, disulphide, sulphoxide, sulphone, tertiary amino, aldehyde, keto, carboxylic ester, carbonate, cyano, alkylsilane and alkoxysilane groups, and also carboxamide groups of secondary amines.

The invention preferably likewise provides mixtures of compounds of the formulae I to IV, preferably mixtures of compounds of the formula II, more preferably mixtures of compounds of the formulae III and IV which are obtainable by using the appropriate starting compounds V in the mixtures of preparative process which is likewise according to the invention and is described hereinbelow.

The invention further provides a process for preparing compounds I to IV, in which hydroxyl compounds of the formula V:

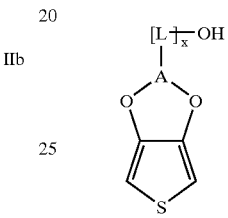

V where
A, x and L are each as defined above are reacted with monoisocyanates, di- and/or higher-functionality isocyanates:

$R(NCO)_n$, where
R and n are each as defined above.

The novel compounds are prepared in a simple manner, in very good and pure yields by reacting compounds or mixtures of compounds of the formula V, more preferably of 2,3-dihydrothieno[3,4-b][1,4]dioxin-2-ylmethanol (alternately referred to hereinbelow as EDT-methanol) and/or 3,4-dihydro-2H-thieno[3,4-b][1,4]dioxepin-3-ol (alternately referred to hereinbelow as hydroxy-PDT), with isocyanates in the approximately stoichiometric OH/NCO ratio of 1:1. When di- or higher-functionality isocyanates are used instead of monoisocyanates, the OH— functional thiophenes may also be used in deficiency, and preferably in such an amount that only one NCO group reacts and all other NCO groups may be utilized for reactions with further NCO-reactive compounds.

In the n-valent isocyanates $R(NCO)_n$ (mono-, di- or higher-functionality isocyanates), R is one of the n-valent radicals already described hereinabove.

The particularly preferred starting compounds EDT-methanol=2,3-dihydrothieno[3,4-b][1,4]dioxin-2-ylmethanol and hydroxy-PDT=3,4-dihydro-2H-thieno[3,4-b][1,4]dioxepin-3-ol can be easily prepared as a mixture according to U.S. Pat. No. 5,111,327. For the preparation of the urethanes according to the invention, preference is given to using such mixtures, more preferably mixtures having EDT-methanol/hydroxy-PDT molar ratios of 90:10 to 65:35.

However, it is also possible to use the pure compounds which are obtainable, for example, by means of chromatographic separation according to U.S. Pat. No. 5,111,327. EDT-methanol may also be prepared directly in pure form according to Reynolds et al., Polym. Prepr. (Am. Chem.

Soc., Div. Polym. Chem.) 38(2), (1997), 320 using 2,3-dibromopropyl acetate.

The hydroxyl compounds of the formula V may generally be prepared in an acid-catalyzed transetherification reaction from alkanetriols and 3,4-dialkoxythiophenes. Useful 3,4-dialkoxythiophenes for this purpose are in particular those having short-chain n-alkoxy groups, preferably methoxy, ethoxy and n-propoxy groups. The principle of this procedure is described in Adv. Mater. 11 (1999), p. 1379–1381. For example, particularly preferred starting compounds of the formula V are accessible by using geminal 1,2-diols which have an additional third hydroxyl group and may be described by way of example by the following formula VI:

HO—CH$_2$—CHOH—(L)$_x$—OH      (VI)

where x and L are each as defined above. It is also possible to prepare EDT-methanol in an alternative to the preparation described in U.S. Pat. No. 5,111,327 by transetherifying 3,4-dialkoxythiophenes with glycerol. Further examples include the preparation of the corresponding compound where x=2 by transetherifying 3,4-dialkoxythiophenes with 1,2,4-butanetriol and of the compound where x=4 by transetherifying 3,4-dialkoxythiophenes with 1,2,6-hexanetriol. The by-products which may be obtained from the transetherification reaction with 1,2,4-butanetriol likewise include the compounds according to the invention of the formula V, 3,4-dihydro-2H-thieno[3,4-b][1,4]dioxepin-2-ylmethanol and 2,3,4,5-tetrahydrothieno[3,4-b][1,4]dioxocin-3-ol. The pure compounds in each case may be isolated by means of chromatographic separation from the mixtures which may be obtained.

Apart from the known compounds of the formula V where x=0 or 1, for example EDT-methanol and hydroxy-PDT, the compounds of the formula V have hitherto not been described in the literature and are also inaccessible by the process according to U.S. Pat. No. 5,111,327. However, they could surprisingly be prepared in a simple manner by the process described in the section hereinabove.

The invention therefore further provides hydroxyl compounds of the formula V or mixtures of hydroxyl compounds of the formula V:

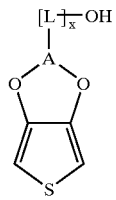

V where
A is a C$_1$–C$_5$-alkylene radical, preferably a C$_2$–C$_3$-alkylene radical, which is optionally substituted at any desired point via a linker L by a hydroxyl group and optionally bears further substituents,
L is a methylene group and
x is an integer greater than 1, preferably an integer from 2 to 6.

Useful A substituents include those already specified above.

The invention further provides a process for preparing oligo- and poly(alkylenedioxythiophene)s having urethane-containing side groups, characterized in that compounds of the formulae I to IV are polymerized. These may be, for example, oxidatively or electrochemically polymerized, but preferably oxidatively polymerized. It is possible to polymerize in each case either one compound selected from the formulae I to IV or mixtures thereof, preferably compounds or mixtures of compounds of the formula II, more preferably compounds or mixtures of compounds of the formula III and/or IV. An example of a further possibility is the halogenation of the monomers of the formulae I to IV to give the corresponding 2,5-dichloro- or 2,5-dibromo(alkylenedioxy)thiophenes and the subsequent reductive polycondensation with Ni(0) compounds, for example Ni-COD compounds.

The process according to the invention provides both homopolymers and copolymers and the corresponding oligomers.

Oligo- and poly(alkylenedioxythiophene)s include all compounds in which more than one unit of the compounds according to the formulae I to IV are linked to one another by polymerization or polycondensation, i.e. have a degree of polymerization of 2. The transition from the oligo- to the poly(alkylenedioxy-ythiophene)s with regard to the degree of polymerization is fluid.

The term "urethane-containing side groups" is to be understood as meaning that the urethane group as a substituent in the alkylenedioxythiophene units is bonded to the alkylene radical A at any desired point either via a linker L or without this linker L in the way represented in formula I, where A and L are each as defined above.

The invention further provides oligo- and poly(alkylenedioxythiophene)s having urethane-containing side groups which are obtainable by polymerizing at least one of the compounds according to the invention of the formulae I to IV.

In a preferred embodiment, these are oligo- and poly(alkylenedioxythiophene)s which have urethane-containing side groups and contain repeating units of the following formula VII:

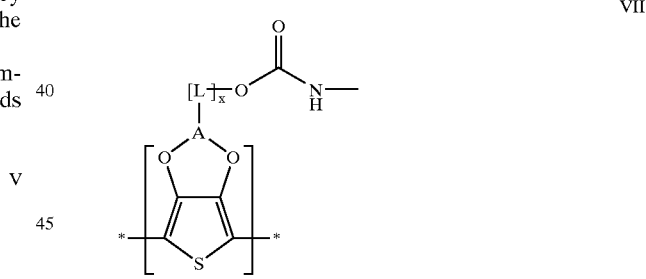

VII where
A, L and x are each as defined above, and, within a polymer, may each independently be the same or different.

For example, based on compounds of the formula I where n=1, these may be oligo- and poly(alkylenedioxythiophene)s of the following formula VIII:

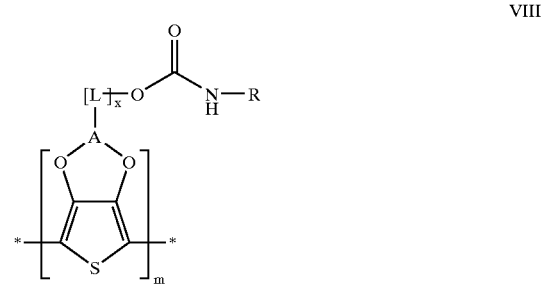

VIII where

R, A, L and x are each as defined above and, within a polymer, may each independently be the same or different, and m is at least 2, preferably at least 2 and at most 2000, more preferably at least 3 and at most 50.

The invention preferably provides oligo- and poly(alkylenedioxythiophene)s which have urethane-containing side groups and contain repeating units of the formulae VIa and/or VIb:

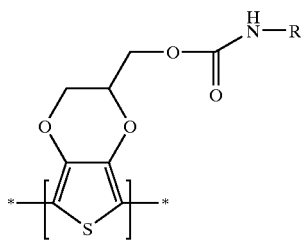

VIa

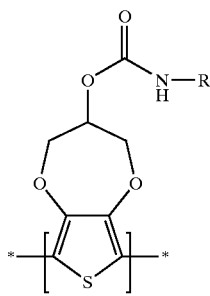

VIb where

R is a linear or branched, optionally substituted $C_1$–$C_{22}$-alkyl radical, an optionally substituted $C_3$–$C_{12}$-cycloalkyl radical or an optionally substituted $C_6$–$C_{14}$-aryl radical, preferably a linear $C_1$–$C_{12}$-alkyl radical or a $C_6$–$C_{10}$-cycloalkyl radical, more preferably a linear $C_4$–$C_{10}$-alkyl radical, and the number of repeating units VIa and/or VIb is at least 2.

These are preferably oligo- and poly(alkylenedioxythiophene)s having urethane-containing side groups where the number of units of the formula VIa and the number of units of the formula VIb are each independently 0 to 1000, with the proviso that the sum of the number of repeating units of the formulae VIa and/or VIb in the oligo- and poly(alkylenedioxythiophene) is at least 2 and at most 2000.

These are more preferably oligo- and poly(alkylenedioxythiophene)s having urethane-containing side groups where the number of units of the formula VIa is 1 to 50 and, independently thereof, the number of units of the formula VIb is 0 to 30, with the proviso that the sum of the number of repeating units of the formulae VIa and/or VIb in the oligo- and poly(alkylenedioxythiophene) is at least 3 and at most 50.

The two different thiophene monomers may be arranged in blocks, alternately or in an uncontrolled, random sequence, but preferably in an uncontrolled, random sequence in the oligomer and polymer.

A route which leads in particular to the above-described poly(alkylenedioxythiophene)s in neutral form is the reductive polycondensation of 2,5-dihalo(alkylenedioxy)thiophenes which are obtainable, for example, by halogenating the monomers of the formulae I to IV. Oxidative polymerization of the compounds of the formulae I to IV using an oxidizing agent are known to those skilled in the art. For example iron-III chloride or iron-III tosylate, may provide either the neutral or the cationic oligo- and poly(alkylenedioxythiophene)s. Under the oxidative polymerization conditions, in particular when there is an excess of oxidizing agent, the oxidation to the highly conductive oligo- and poly(alkylenedioxythiophene) polycation may be effected as early as this stage.

Alternatively, the cationic oligo- and poly(alkylenedioxythiophene)s may also be prepared by subsequent oxidation of the neutral poly(alkylenedioxythiophene)s with the aid of oxidizing agents known to those skilled in the art.

The invention therefore likewise provides oligo- and poly(alkylenedioxythiophene)s having urethane-containing side groups prepared from at least one compound of the formulae I to IV, characterized in that they bear positive charges. The number of positive charges may be at least 1 and at most the number of alkylenedioxythiophene units.

For example, based on compounds of the formula I wherein n=1, there are provided oligo- and poly(alkylenedioxythiophene)s of the following formula IX:

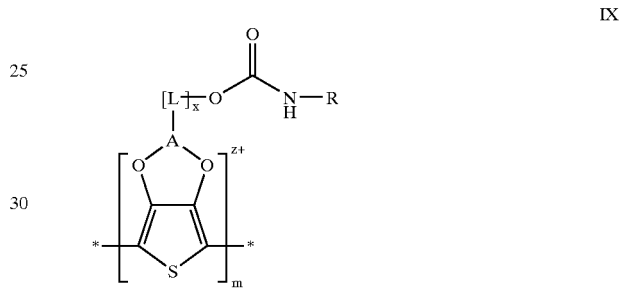

IX which carry z positive charges, where the number of z positive charges is at least 1 and is at most the number of repeating units m, preferably at least 1 and at most m=2, more preferably at least 1 and at most m=3 to m=4. To neutralize the z positive charges, there is a number z of counterions (anions) or an oligo- or polyanion having z negative charges, or optionally both together in a mixture, in the presence of the oligo- and poly(alkylenedioxythiophene) cation. Examples of oligo- or polyanions include those of oligo- and polymeric carboxylic or sulphonic acids, for example polyacrylic acids or polystyrenesulphonic acids. The oligo- and poly(alkylenedioxythiophene) cations and oligo- and polyanions may be together, for example, in a solid, in solution or in dispersion.

The positive charges of the polythiophenepolycations generated by oxidation during or after polymerization are not represented in the formulae, since the exact number and position thereof cannot be definitively established.

The invention also provides two- or three-dimensionally crosslinked neutral or cationic oligo- and poly(alkylenedioxythiophene)s, characterized in that they are obtainable by oxidative polymerization from at least one of the compounds of the formulae I to IV, preferably from compounds or mixtures of compounds of the formula II, more preferably from compounds of the formulae IIa and/or IIb.

Surprisingly, the oligo- and poly(alkylenedioxythiophene)s having urethane-containing side groups according to the invention exhibit a high conductivity in comparison to known compounds, without losing transparency. Owing to these advantageous properties, they are particularly suitable for use in electronic and electrical components.

The invention therefore further provides the use of the oligo- and poly(alkylenedioxythiophene)s according to the invention as constituents in electronic or electrical components.

In the practice of the invention, the monomers I–IV, the neutral oligomers and polymers which are prepared from them and also the cationic polymers may serve to produce organic electrical or electronic components. Examples thereof are for producing lighting elements, photocells or organic transistors, for treating plastic films for packing electronic components and for clean-room packagings, for antistatically treating cathode ray tubes, for antistatically treating photographic films, as transparent heating, as transparent electrodes, as circuit boards or for electrically colourable window panes. Oxidative polymerization allows, for example, conductive layers to be generated on non-conductive substrates, such as glass, ceramic, plastic, etc. In capacitors, the layers generated in this way can take on the role of the cathode.

The compounds of the formulae I to IV may be applied to the substrates in a mixture with the oxidizing agent from organic solvents, for example alcohols, methylene chloride, chloroform, N-methylpyrrolidone, etc., by knife coating, spin coating, pouring, impregnating, etc.

The examples which follow but are not to be interpreted as a limitation show that the oligo- and poly(alkylenedioxythiophene)s having urethane-containing side groups according to the invention having distinctly improved conductivities in comparison to known compounds can be produced.

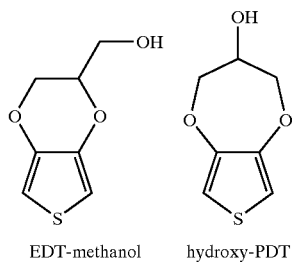

EDT-methanol    hydroxy-PDT

The 80:20 EDT-methanol/hydroxy-PDT mixture used in the following was prepared according to U.S. Pat. No. 5,111,327.

EXAMPLE 1

13.0 g of 80:20 EDT-methanol/hydroxy-PDT mixture were dissolved in 20 ml of absolute (abs.) toluene under $N_2$. 7.48 g of n-butyl isocyanate were rapidly added dropwise with stirring at room temperature (23° C.). The reaction mixture was then heated to 100° C. for 2 h. According to thin layer chromatography (eluent chloroform/methanol 10:1), the reaction was then complete. After cooling to room temperature, the mixture was stirred with 20 ml of methanol for a few min.; all solvents were then removed at 20° C./20 mbar. The oily residue was purified on a silica gel column using $CHCl_3$/ethyl acetate 1:1 as the eluent. 3.3 g of pure and also 14.4 g of slightly contaminated product were obtained, total yield: 86.4% of theory. For further investigations and reactions, the pure fraction was always used.

EXAMPLE 2

12.0 g of 80:20 EDT-methanol/hydroxy-PDT mixture were dissolved in 20 ml of abs. toluene under $N_2$. 8.86 g of n-hexyl isocyanate were rapidly added dropwise with stirring at room temperature (23° C.). The reaction mixture was then heated to 100° C. for 11.5 h. According to thin layer chromatography (eluent toluene/ethyl acetate 1:1), the reaction was then complete. After cooling to room temperature, the mixture was stirred with 25 ml of methanol for a few min.; all solvents were then distilled off at 20 mbar. The oily residue was purified on a silica gel column using toluene/ethyl acetate 1:1 as the eluent. 14.27 g of product which was pure according to $^1H$ NMR were obtained, yield: 68.4% of theory.

EXAMPLE 3

12.0 g of 80:20 EDT-methanol/hydroxy-PDT mixture were dissolved in 20 ml of abs. toluene under $N_2$. 10.82 g of n-octyl isocyanate were rapidly added dropwise with stirring at room temperature (23° C.). The reaction mixture was then heated to 100° C. for 7.5 h. According to thin layer chromatography (eluent hexane/toluene 1:1), the reaction was then complete. After cooling to room temperature, the mixture was stirred with 25 ml of methanol for a few min.; all solvents were then distilled off at 20 mbar. Residue: 20.0 g of oily product, yield: 87.6% of theory.

EXAMPLE 4

10.0 g of 80:20 EDT-methanol/hydroxy-PDT mixture were dissolved in 20 ml of abs. toluene under $N_2$. 12.72 g of n-dodecyl isocyanate were within 30 min. added dropwise with stirring at room temperature (23° C.). The reaction mixture was then heated to 70° C. for 7 h and maintained at 80° C. for a further 16 h. After cooling to room temperature, the precipitated product was recrystallized from 30 ml of methanol and washed with 10 ml of methanol. Yield 19.0 g=85.3% of theory; according to $^1H$ NMR, 78% of dodecylurethane of EDT-methanol and 22% of dodecylurethane of hydroxy-PDT.

EXAMPLE 5

8.0 g of 80:20 EDT-methanol/hydroxy-PDT mixture were dissolved in 20 ml of abs. toluene under $N_2$. 13.73 g of n-octadecyl isocyanate were within 30 min. added dropwise with stirring at room temperature (23° C.). The reaction mixture was then stirred at 100° C. for 7.5 h. According to thin layer chromatography (eluent toluene/hexane 1:1), the reaction was then complete. After cooling to room temperature, the precipitated product was stirred with 25 ml of methanol; all solvents were then removed at 20° C./20 mbar and the residue was recrystallized from methanol. Yield 16.15 g=74.3% of theory.

EXAMPLE 6

12.0 g of 80:20 EDT-methanol/hydroxy-PDT mixture were dissolved in 20 ml of abs. toluene under $N_2$. 8.72 g of cyclohexyl isocyanate were rapidly added dropwise with stirring at room temperature (23° C.). The reaction mixture was then stirred at 100° C. for 2 h. According to thin layer chromatography (eluent chloroform/methanol 10:1), the reaction was then complete. After cooling to room temperature, the mixture was stirred with 20 ml of methanol; all solvents were then removed at 20° C./20 mbar. The residue was triturated with petroleum benzine and the solid product filtered off with suction. Yield 17.5 g=84.5% of theory.

EXAMPLE 7

12.0 g of 80:20 EDT-methanol/hydroxy-PDT mixture were dissolved in 20 ml of abs. toluene under $N_2$. 8.3 g of phenyl isocyanate were rapidly added dropwise with stirring at room temperature (23° C.). The reaction mixture was then stirred at approx. 100° C. for 3.5 h. According to thin layer chromatography (eluent chloroform/methanol 10:1), the reaction was then complete. After cooling to room temperature, the semicrystalline mixture was stirred with 25 ml of methanol and the solid was filtered off with suction. Yield=2.3 g of product (white crystals). A further 1.5 g of solid product were isolated from the mother liquor by precipitating with methanol. The mother liquor which then remained was concentrated by evaporation and purified on a silica gel column using toluene as the eluent. Overall yield quantitative.

EXAMPLE 8

13.0 g of 80:20 EDT-methanol/hydroxy-PDT mixture were dissolved in 20 ml of abs. toluene under $N_2$. 7.48 g of tert-butyl isocyanate were rapidly added dropwise with stirring at room temperature (23° C.). The reaction mixture was then heated to approx. 100° C. for 7.5 h. After cooling to room temperature, the mixture was stirred with 25 ml of methanol for a few min.; all solvents were then removed at 20° C./20 mbar. The oily residue was purified on a silica gel column using $CHCl_3$/ethyl acetate 1:1 as the eluent. 1.51 g=7.4% of theory of product were obtained as a light yellow oil. According to $^1H$ NMR, there was 93% of the tert-butylurethane of EDT-methanol and 7% of the tert-butylurethane of hydroxy-PDT.

EXAMPLE 9

8.0 g of 80:20 EDT-methanol/hydroxy-PDT mixture were dissolved in 20 ml of abs. toluene under $N_2$. 5.16 g of isophorone diisocyanate were rapidly added dropwise with stirring at room temperature (23° C.) (NCO/OH=1.1). The reaction mixture was then heated to 100° C. for 5.5 h. After cooling to room temperature, the mixture was stirred with 25 ml of methanol for a few min.; all solvents were then removed at 20° C./20 mbar. Yield quantitative.

EXAMPLE 10

16.0 g of 80:20 EDT-methanol/hydroxy-PDT mixture were dissolved in 20 ml of abs. toluene under $N_2$. 7.8 g of isocyanatoacetate were rapidly added dropwise with stirring at room temperature (23° C.). The reaction mixture was then heated to 100° C. for 32 h. According to thin layer chromatography (eluent toluene/ethyl acetate 1:1), the reaction was then complete. After cooling to room temperature, the mixture was stirred with 20 ml of methanol for a few min.; all solvents were then distilled off at 20 mbar. The oily residue was purified on a silica gel column using toluene/ethyl acetate 1:1 as the eluent. 10.95 g of product which was pure according to $^1H$ NMR were obtained as an orange-brown, viscous liquid, yield: 96.3% of theory.

EXAMPLE 12

5.0 g of 80:20 EDT-methanol/hydroxy-PDT mixture were dissolved in 10 ml of abs. toluene under $N_2$. 7.18 g of 3-(triethoxysilyl)propyl isocyanate were rapidly added dropwise with stirring at room temperature (23° C.). The reaction mixture was then heated to 100° C. for 19 h. According to thin layer chromatography (eluent toluene/ethyl acetate 1:1), the reaction was then complete. After cooling to room temperature, the mixture was stirred with 20 ml of ethanol for a few min.; all solvents were then distilled off at 20 mbar. Residue: 11.86 g of oily, orange-coloured product which is pure according to the $^1H$ NMR spectrum, yield: 97.4% of theory.

EXAMPLE 13

The following procedure was used to produce cationic polymers as coatings on glass from compounds according to the invention and also from comparative compounds according to U.S. Pat. No. 5,111,327 and 3,4-ethylenedioxythiophene:

14 mmol of the thiophene compound are mixed with 50 g of a 40% solution of Fe-III tosylate in n-butanol and 212 g of n-butanol. The solution is applied to glass using a doctor blade at a wet film thickness of 60 μm and dried at the specified temperature for the specified time. The conductive polymer film is then washed with deionized water. The surface resistances are measured after drying and, if necessary, cooling to 23° C. by the two-point method with the aid of conductive silver contacts. The polymerization begins slowly as soon as mixing is effected and is completed after the specified drying time.

| Thiophene compound | Drying Temperature | Drying time | Surface resistance (at 23° C.) | |
|---|---|---|---|---|
| Example 1 | 40° C. | 10 min | 25 Ohm/sq | (inventive) |
| Example 2 | 40° C. | 10 min | 33 Ohm/sq | (inventive) |
| Example 3 | 23° C. | 20 min | 23 Ohm/sq | (inventive) |
| Example 9 | 40° C. | 10 min | 26 Ohm/sq | (inventive) |
| EDT-Methanol/Hydroxy-PDT 8:2 | 40° C. | 10 min | 43 Ohm/sq | (comparative) |
| Ex. 7 from US-A 5.111.327 | 40° C. | 10 min | 70 Ohm/sq | (comparative) |
| 3,4-Ethylenedioxythiophene | 40° C. | 10 min | 40 Ohm/sq | (comparative) | hexamethylene diisocyanate were rapidly added dropwise with stirring at room temperature (23° C.) (NCO/OH=1.1). The reaction mixture was then heated to approx. 100° C. for 7.5 h. After cooling to room temperature, the mixture was stirred with 25 ml of methanol for a few min. 5.1 g=21.4% of theory of product precipitated as colourless crystals.

EXAMPLE 11

6.5 g of 80:20 EDT-methanol/hydroxy-PDT mixture were dissolved in 10 ml of abs. toluene under $N_2$. 4.87 g of ethyl The results show the compounds according to the invention exhibit lower surface resistances and therefore higher conductivities than the existing comparative compounds investigated.

EXAMPLE 14

4.532 g of iron-III chloride are initially charged in 100 ml of chloroform. 3.293 g of the urethane prepared in Example 2 are metered in and the mixture is stirred at room temperature (23° C.) for 16 h. The reaction mixture is then precipitated into a mixture of 100 ml of methylene chloride and 50 ml of 26% ammonia. The ammonia phase is removed and replaced by fresh ammonia. This procedure is repeated twice. The organic phase is then removed and extracted with 0.05 molar aqueous EDTA solution. The organic phase is then washed three times with water and then dried over $Na_2SO_4$. After concentration in a water jet vacuum to half of the volume, the product is precipitated by pouring into a mixture of 220 ml of methanol and 33 ml of 26% ammonia. The solid which has been filtered off with suction is dissolved at a concentration of 1.4% in tetrahydrofuran (deep red-violet solution) and then deionized in the protonated form with 10 g of an acidic ion exchanger based on styrene/divinylbenzene for 2 h.

This gave the neutral polymer of the thiophene derivative from Example 2.

EXAMPLE 15

4.116 g of iron-III chloride are initially charged in 100 ml of chloroform. 3.27 g of the urethane prepared in Example 3 are metered in and the mixture is stirred at room temperature (23° C.) for 16 h. The reaction mixture is then precipitated into a mixture of 100 ml of methylene chloride and 50 ml of 26% ammonia. The ammonia phase is removed and replaced by fresh ammonia. This procedure is repeated twice. The organic phase is then removed and extracted with 0.05 molar aqueous EDTA solution. The organic phase is then washed three times with water and then dried over $Na_2SO_4$. After concentration in a water jet vacuum to half of the volume, the product is precipitated out by pouring into a mixture of 220 ml of methanol and 33 ml of 26% ammonia. The solid which has been filtered off with suction (0.7 g) is dissolved at a concentration of 2.16% in tetrahydrofuran (deep red-violet solution) and then deionized in the protonated form with 10 g of an acidic ion exchanger based on styrene/divinylbenzene for 2 h.

This gave the neutral polymer of the thiophene derivative from Example 3.

According to GPC (polystyrene calibration, RI (refractive index) detection), the molecular weight (weight average) is $M_w$=12,200.

Examples 14 and 15 show the possibility of targeted preparation of the neutral polymers by the route of oxidative polymerization which has already been described hereinabove.

General Method for Synthesizing the Hydroxyl Compounds of the General Formula V

For example, the hydroxyl compounds of the general formula V may be synthesized by transetherification by heating 3,4-di-n-propoxythiophene and an alkanetriol, preferably the alkanetriol in excess, with p-toluenesulphonic acid as the catalyst under $N_2$ for 2 h (or longer) while slowly distilling off n-propanol. After cooling, the remaining liquid is diluted with methylene chloride, washed to neutrality with water and the organic phase is dried over $Na_2SO_4$. After removing the solvent, the hydroxyl compound of the general formula V is obtained.

EXAMPLE 16

Preparation of 2-(2,3-dihydrothieno[3,4-b][1,4]dioxin-2-yl) ethanol 9.06 g (45.2 mmol) of 3,4-di-n-propoxythiophene, 24.0 g (226 mmol) of 1,2,4-butanetriol and 0.09 g (0.5 mmol) of p-toluenesulphonic acid were heated to 150 to 160° C. (bath temperature) under $N_2$ for 2 h. During this time, 5.89 g of distillate (substantially n-propanol) were collected. The cooled liquid was diluted with 50 ml of methylene chloride, washed to neutrality with water and the organic phase was dried over $Na_2SO_4$. After filtering and evaporating the methylene chloride at 1 mbar, distillation was then effected. According to $^1$H NMR spectroscopy, the fraction collected between 45 and 128° C. (1.63 g=19.4% of overall theoretical yield of transetherification products) consisted of approx. 81.5% of 2-(2,3-dihydrothieno[3,4-b][1,4]dioxin-2-yl) ethanol, 6.5% of 3,4-dihydro-2H-thieno[3,4-b][1,4] dioxepin-2-ylmethanol and 12% of 2,3,4,5-tetrahydrothieno [3,4-b][1,4]dioxocin-3-ol.

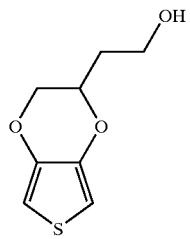

2-(2,3-Dihydrothieno[3,4-b]
[1,4]dioxin-2-yl)ethanol

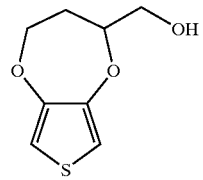

3,4-Dihydro-2H-thieno[3,4-b]
[1,4]dioxepin-2-ylmethanol

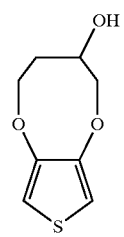

2,3,4,5-Tetrahydrothieno[3,4-b]
[1,4]dioxocin-3-ol

EXAMPLE 17

Preparation of 4-(2,3-dihydrothieno[3,4-b][1,4]dioxin-2-yl)-1-butanol.

9.06 g (45.2 mmol) of 3,4-di-n-propoxythiophene, 30.3 g (226 mmol) of 1,2,6-hexanetriol and 0.09 g (0.5 mmol) of p-toluenesulphonic acid are heated to 150 to 165° C. (bath temperature) under $N_2$ for 3 h. During this time, 5.8 g of distillate (substantially n-propanol) were collected. The cooled liquid was diluted with 50 ml of methylene chloride, washed to neutrality and to free it of hexanetriol with water and the organic phase was dried over $Na_2SO_4$. After filtering and evaporating the methylene chloride, the residue (6.73 g=74.8% of theory) was identified by $^1$H NMR spectroscopy (in $CDCl_3$ against TMS) using δ=6.30 ppm (2H, thiophene H) and 2.85 ppm (1H, OH) as being substantially 4-(2,3-dihydrothieno[3,4-b][1,4]dioxin-2-yl)-1-butanol.

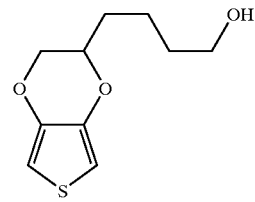

4-(2,3-Dihydrothieno[3,4-b]
[1,4]dioxocin-2-yl)-1-butanol

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Compounds of the formula I:

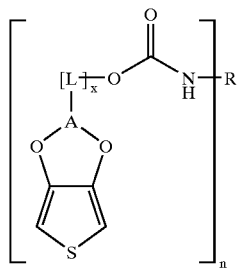

characterized in that

A is a $C_1$–$C_5$-alkylene radical which is optionally substituted at any desired point via a linker L by a urethane group and optionally bears further substituents, L is a methylene group, x is 0 or an integer of 1 or greater, n is an integer from 1 to 4 and R is an n-valent linear or branched, optionally substituted, aliphatic $C_1$–$C_{22}$ radical, an n-valent, optionally substituted, cycloaliphatic $C_3$–$C_{12}$ radical or an n-valent, optionally substituted, aromatic $C_6$–$C_{14}$ radical, where, in the case that n is greater than 1, A and x is optionally each independently defined identically or differently.

2. Compounds of the formula I according to claim 1, characterized in that x is 0 or an integer from 1 to 6.

3. Compounds of the formula I according to claim 1:

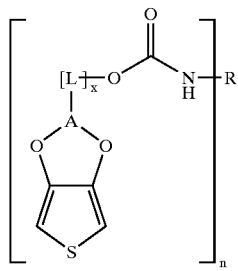

characterized in that

A is a $C_1$–$C_5$-alkylene radical which is optionally substituted at any desired point via a linker L by a urethane group and optionally bears further substituents, L is a methylene group, x is 0 or 1, n is an integer from 1 to 4 and R is an n-valent linear or branched, optionally substituted, aliphatic $C_1$–$C_{22}$ radical, an n-valent, optionally substituted, cycloaliphatic $C_3$–$C_{12}$ radical or an n-valent, optionally substituted, aromatic $C_6$–$C_{14}$ radical, where, in the case that n is greater than 1, A and x is optionally each independently defined identically or differently.

4. Compounds of the formula II according to claim 1:

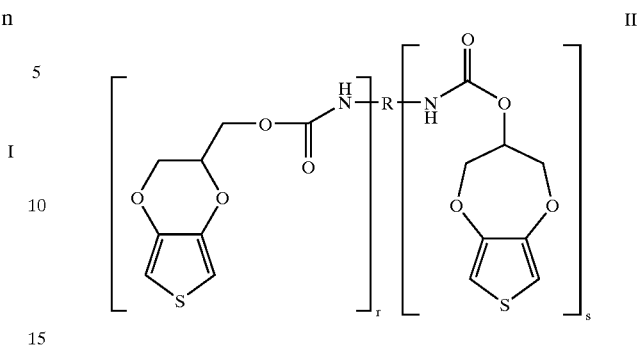

characterized in that

R is an n-valent linear or branched, optionally substituted, aliphatic $C_2$–$C_{22}$ radical, an n-valent, optionally substituted, cycloaliphatic $C_5$–$C_{12}$ radical or an n-valent, optionally substituted, aromatic $C_6$–$C_{14}$ radical, r and s are each independently integers from 0 to 4, with the proviso that r+s=n and n is an integer from 1 to 4.

5. Compounds according to at claim 1, characterized in that R is a linear, optionally substituted $C_6$–$C_{12}$-alkylene radical or an optionally substituted $C_6$–$C_{10}$-cycloalkylene radical, and r and s are each independently integers from 0 to 2 and n=r+s=2.

6. Compounds according to claim 1 of the formulae III and/or IV:

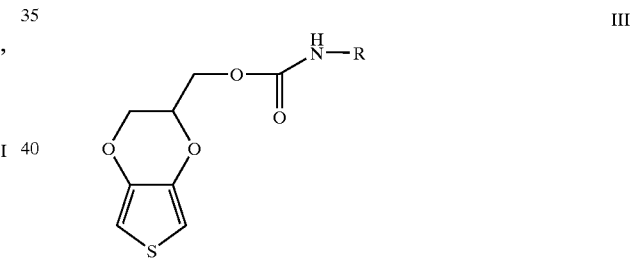

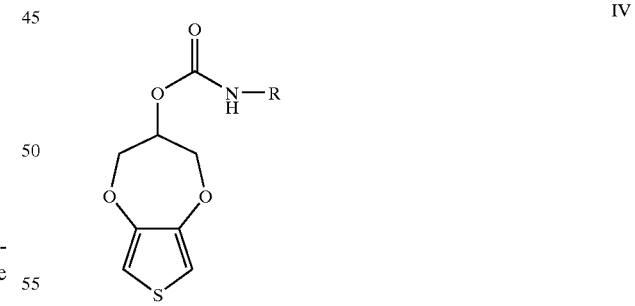

characterized in that

R is a linear or branched, optionally substituted, $C_1$–$C_{22}$-alkyl radical, an optionally substituted, $C_3$–$C_{12}$-cycloalkyl radical or an optionally substituted, $C_6$–$C_{14}$-aryl radical.

7. Compounds according to claim 1, characterized in that R is a linear $C_1$–$C_{12}$-alkyl radical or a $C_6$–$C_{10}$-cycloalkyl radical.

8. Compounds according to claim 1, characterized in that R is a linear $C_4$–$C_{10}$-alkyl radical.

9. Process for preparing compounds of the formulae I to IV, comprising reacting hydroxyl compounds of the formula V:

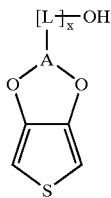

V where

A, x and L are each as defined in claim 1 with monoisocyanates, diisocyanates, higher-functionality isocyanates, or mixtures thereof, represented as:

where

R and n are each as defined in claims 1 to 8.

10. Process for preparing oligo- and poly(alkylenedioxythiophene)s having urethane-containing side groups, comprising polymerizing compounds of the formulae I to IV.

11. Oligo- and poly(alkylenedioxythiophene)s having urethane-containing side groups, characterized in that they are obtainable by polymerizing at least one compound according to claim 1.

12. Oligo- and poly(alkylenedioxythiophene)s having urethane-containing side groups according to claim 11, characterized in that they contain repeating units of the formulae VIa and/or VIb:

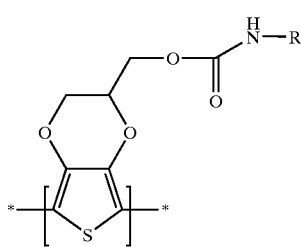

VIa

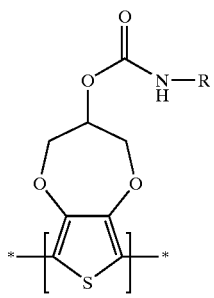

VIb where

R is as defined in at least one of claims 1 to 8 and the number of repeating units VIa and/or VIb is at least 2.

13. Oligo- and poly(alkylenedioxythiophene)s having urethane-containing side groups according to claim 11, characterized in that the number of units of the formula VIa and the number of units of the formula VIb are each independently 0 to 1000, with the proviso that the sum of the number of repeating units of the formulae VIa and/or VIb in the oligo- or poly(alkylenedioxythiophene) is at least 2 and at most 2000.

14. Oligo- and poly(alkylenedioxythiophene)s having urethane-containing side groups according to claim 11, characterized in that the number of units of the formula VIa is 1 to 50 and, independently thereof, the number of units of the formula VIb is 0 to 30, with the proviso that the sum of the number of repeating units of the formulae VIa and/or VIb in the oligo- or poly(alkylenedioxythiophene) is at least 3 and at most 50.

15. Oligo- and poly(alkylenedioxythiophene)s having urethane-containing side groups according to claim 11, characterized in that they carry positive charges.

16. Two- or three-dimensionally crosslinked neutral or cationic oligo- and poly(alkylenedioxythiophene)s having urethane-containing side groups, characterized in that they are obtainable by oxidative polymerization of the compounds according to claim 1.

17. A method of preparing an electrical component comprising providing as constituent thereof the oligo- and poly(alkylenedioxythiophene)s according to claim 11.

18. Hydroxyl compounds of the formula V or mixtures of hydroxyl compounds of the formula V:

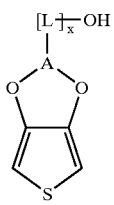

V where

A is a $C_1-C_5$-alkylene radical which is optionally substituted at any desired point via a linker L by a hydroxyl group and optionally bears further substituents, L is a methylene group and x is an integer greater than 1.

19. Hydroxyl compounds of the formula V or mixtures of hydroxyl compounds of the formula V according to claim 18, where x is an integer from 2 to 6.

* * * * *